(12) United States Patent
Meer et al.

(10) Patent No.: US 7,885,379 B2
(45) Date of Patent: Feb. 8, 2011

(54) POSITIONING DEVICE FOR A MAMMOGRAPHY UNIT

(75) Inventors: Oliver Meer, München (DE); Martin Ramsauer, Pyrbaum (DE)

(73) Assignee: Siemens Aktiengesellschaft (DE)

( * ) Notice: Subject to any disclaimer, the term of this patent is extended or adjusted under 35 U.S.C. 154(b) by 32 days.

(21) Appl. No.: 12/162,282

(22) PCT Filed: Jan. 8, 2007

(86) PCT No.: PCT/EP2007/050130
§ 371 (c)(1),
(2), (4) Date: Dec. 12, 2008

(87) PCT Pub. No.: WO2007/090693
PCT Pub. Date: Aug. 16, 2007

(65) Prior Publication Data
US 2009/0304159 A1  Dec. 10, 2009

(30) Foreign Application Priority Data
Feb. 3, 2006 (DE) ........................ 10 2006 005 068

(51) Int. Cl.
*A61B 6/04* (2006.01)
(52) U.S. Cl. ........................................................ 378/37
(58) Field of Classification Search ................. 378/37
See application file for complete search history.

(56) References Cited

U.S. PATENT DOCUMENTS

| | | | |
|---|---|---|---|
| 4,979,196 A | 12/1990 | Lieutaud et al. | |
| 5,018,176 A | 5/1991 | Romeas et al. | |
| 5,820,552 A * | 10/1998 | Crosby et al. | 378/37 |
| 6,882,700 B2 * | 4/2005 | Wang et al. | 378/37 |
| 6,999,554 B2 | 2/2006 | Mertelmeier | |
| 2003/0198315 A1 * | 10/2003 | Andreasson et al. | 378/37 |
| 2005/0100129 A1 | 5/2005 | McKenna | |
| 2005/0113681 A1 | 5/2005 | DeFreitas et al. | |
| 2005/0129172 A1 * | 6/2005 | Mertelmeier | 378/37 |

FOREIGN PATENT DOCUMENTS

| | | |
|---|---|---|
| DE | 101 62 236 A1 | 7/2002 |
| DE | 103 53 611 A1 | 6/2005 |
| WO | WO 90/05485 | 5/1990 |

OTHER PUBLICATIONS

Mammomat Novation, Digital Mammography at its Very Best, 2004, Internet link: http://www.medical.siemens.com/siemens/en_US/gg_sps_FBAs/files/brochures/MAMMOMAT_NovationDR/Mammomat_Novation_USA_Brochure.pdf.
German Office Action dated Nov. 15, 2006 with English translation.
International Search Report dated Jun. 21, 2007 with English translation.
Written Opinion dated Jun. 21, 2007 with English translation.
English translation of the German translation of Chinese Office Action for China Patent Application No. 200780004486.4 dated Feb. 5, 2010.

* cited by examiner

*Primary Examiner*—Chih-Cheng G Kao
(74) *Attorney, Agent, or Firm*—Brinks Hofer Gilson & Lione

(57) ABSTRACT

The present embodiments relate to a mammography unit may be improved, by provision of a positioning device for a mammography unit, comprising a device support section for accommodating the radiation source and an object support device for accommodating the object holder for the relative positioning of a radiation source and an object holder. The object support section may be and/or is connected to the mammography unit by means of a connector element, wherein the device support section is mounted such as to be able to rotate relative to the connector element.

12 Claims, 3 Drawing Sheets

POSITIONING DEVICE FOR A MAMMOGRAPHY UNIT

The present patent document is a §371 nationalization of PCT Application Serial Number PCT/EP2007/050130, filed Jan. 8, 2007, designating the United States, which is hereby incorporated by reference. This patent document also claims the benefit of DE 10 2006 005 068.1, filed Feb. 3, 2006, which is also incorporated by reference.

BACKGROUND

The present embodiments relate to a positioning device for a mammography unit for the relative positioning of a radiation source and an object holder.

Mammography units perform examinations on the soft tissue of the human breast using x-rays and are used for the early diagnosis of breast cancer. Early diagnosis examinations form part of standard preventative medical checkups in some countries of Europe, such as Germany. As a result of the frequency of the mammography examinations and the simultaneous cost pressure in terms of health care, it is necessary to simplify the operation of mammography units and to increase their flexibility of use in order in this way to conserve examination time while retaining or improving examination quality.

Mammography units, such as "Mammomat 1000", "Mammomat 3000 Nova" and "Mammomat Novation", in terms of constructive design, are realized in a similar fashion and are described representationally in the example of the "Mammomat Novation": The mammography unit has a base body and a device arm, which is angled and protrudes from the base body, at the free end of which a radiation source is arranged. The device arm is realized as a sheet metal construction and is connected to an axis of rotation of the mammography unit in a torque-proof fashion. The radiation source can be pivoted about 360° about the isocenter. An object table is mounted on the device arm by way of a rotative connection. The object table is pivotable about 360° about the isocenter.

SUMMARY & DESCRIPTION

The present embodiments may obviate one or more of the drawbacks inherent in the related art. For example, in one embodiment, the robustness and the measurement accuracy of a mammography unit may be improved using a positioning device.

The positioning device is suited to and/or embodied for a mammography unit and is used for the relative positioning of a radiation source and an object holder. The radiation source emits soft x-rays in the range of below 50 kV (Kilovolt), for example, below 30 kV. The object holder accommodates a female breast, subsequently also referred to as examination object, with the object holder including a facility for compressing the breast. The object holder may include an object table and a compression plate, which can be displaced against examination object. A device support section and an object support section accommodate the radiation source and/or the object holder. The object support section can be and/or is connected to the mammography unit by a connecting element.

The device support section is mounted, such as to be able to rotate relative to the connecting element, for example, relative to the object support section and/or the mammography unit. The device support section is mounted, such as to be able to rotate irrespective of and/or decoupled from the object support section. The device support section may be rotatably mounted on the connecting element.

It may be disadvantageous to mount the object support section on an axis of rotation, which is fixedly connected to the device support section, since with examinations, in which different irradiation angles of the x-rays are required, a change in position of the device support section can result in an adjustment of the object support section.

The object support section is mounted on the device support section. The device support section is mounted such as to be able to rotate relative to the connecting element between the mammography unit and the object support section. The examination object may be radiated from different irradiation directions, without the position of the object support section and the examination object changing with a change in position of the device support section. Accordingly, sections of the open kinematics chain are remodeled.

In one embodiment, the device support section is embodied as a device arm and has a free end and an end hinged to the connecting element. The free end accommodates the radiation source and if applicable further components, such as a diaphragm or electronics system. The hinged end surrounds the connecting element at least in sections and/or has a through opening or receiving opening, through which the connecting element protrudes at least in sections. In this embodiment, the lifting arm from the mammography unit to the radiation source is divided into two sections, with the first section being formed by the connecting element and the second section being formed by the device section. The connecting element may have a diameter of at least 10 cm, preferably at least 15 cm, in particular at least 20 cm in a region on which the device support section is mounted and/or supported. The device support section is compact, so that the positioning device is itself stable and less prone in terms of oscillations of the radiation source.

A counterweight may be arranged on the hinged end with respect to the device arm, such that a counter torque is formed with respect to the device arm. The device arm and counterweight may be arranged diametrally relative to one another in respect of the through opening and/or receiving opening.

In one embodiment, the hinged end is embodied as an annular or toroidal body, which forms the through opening or receiving opening.

In one embodiment, the connecting element may be embodied as an axis of rotation and/or swivel axis for the object support section and allows a rotation of the object support section. The object support section is connected to the axis of rotation and/or swivel axis in a torque-proof fashion and rotates together with this or is rotatably mounted on the particularly stationary axis of rotation and/or swivel axis.

The object support section includes a second body, which is embodied as a cover element and upon which the connecting element rests, for example, upon the axis of rotation and/or swivel axis. Alternatively, the second body is annular or toroidal. The first body may be arranged between the mammography unit and the second body and/or is arranged accordingly when the positioning device is operated. When the radiation source is rotated during an examination, the rotation source rotates behind the second body, as viewed from the patient's perspective, and is covered by the first body. The risk of crushing for operator and patient is minimized in this way.

The first and second bodies are congruent at least in sections in the direction of the longitudinal extension of the connecting element and/or to be flush with one another perpendicular to the longitudinal extension. Accordingly, the risk of crushing is further minimized. The first and second bodies together preferably form a closed, circular external contour.

The first and second bodies remain congruent and/or flush with one another during a rotation of the device support section and/or object support section.

In one embodiment, the device support section and object support section are arranged, such as to be able to rotate about a common axis of rotation. The common axis of rotation is parallel to the longitudinal extension of the connecting element.

The common axis of rotation may lead through a common isocenter, which is arranged in the center of the subsequent examination object, which is positioned there for examination purposes. The radiation source and object holder are rotatably mounted so that the position of the examination object does not have to be changed even when the irradiation angle of the radiation source and/or of the attack angle of the object holder changes. One benefit of the isocentric arrangement of the device support section and object support section is that the mammography device only has to be adjusted to the patient once.

With a preferred development of the positioning device, the device support section can be pivoted relative to the object support by up to +/−25°. This swivel angle allows the irradiation angle to be changed for stereotactic examinations that have swivel angles of +/−10° and/or +/−15°. The positioning device also allows tomosynthesis examinations, in which a continuous swiveling of the radiation source of up to +/−25° may be needed in order to generate a tomography exposure of the examination object. In the case of steriotaxy and tomosynthesis, the device support section may be rotatably or pivotably mounted irrespective of or decoupled from the object support section.

The connecting element embodied an axis of rotation or swivel axis allows a rotation and/or swiveling of the object support section of up to +/−180°. The examination object may be photographed in standard views like, for instance, a craniocaudal (CC) or mediolateral oblique (MLO) view.

In order to individually adjust the mammography device to the respective patient, provision is made for the connecting element and the device support section and the object support section to be embodied so as to be adjustable in terms of height and/or lateral position in respect of the mammography unit. The height adjustment allows the mammography unit to be adjusted to different patient body sizes in a user-friendly fashion.

With a preferred embodiment of the positioning device, displays, control elements, or levers are arranged on the object support section and/or the device support section, for example, on the first and/or second body. As a result of an optional concentric arrangement of the control elements on the first and/or second body, it is possible to conveniently access the control elements from all usual positions or adjustments (ML, ML0 etc.) of the positioning device.

The setting of the positioning device, such as the rotation or swiveling of the device support section and/or the object support section, either takes place manually or in a motor-driven fashion. The described positioning device is particularly suited to a diagnostic method for an x-ray examination of an examination object, in particular for mammography.

DETAILED DESCRIPTION

Figure 1:
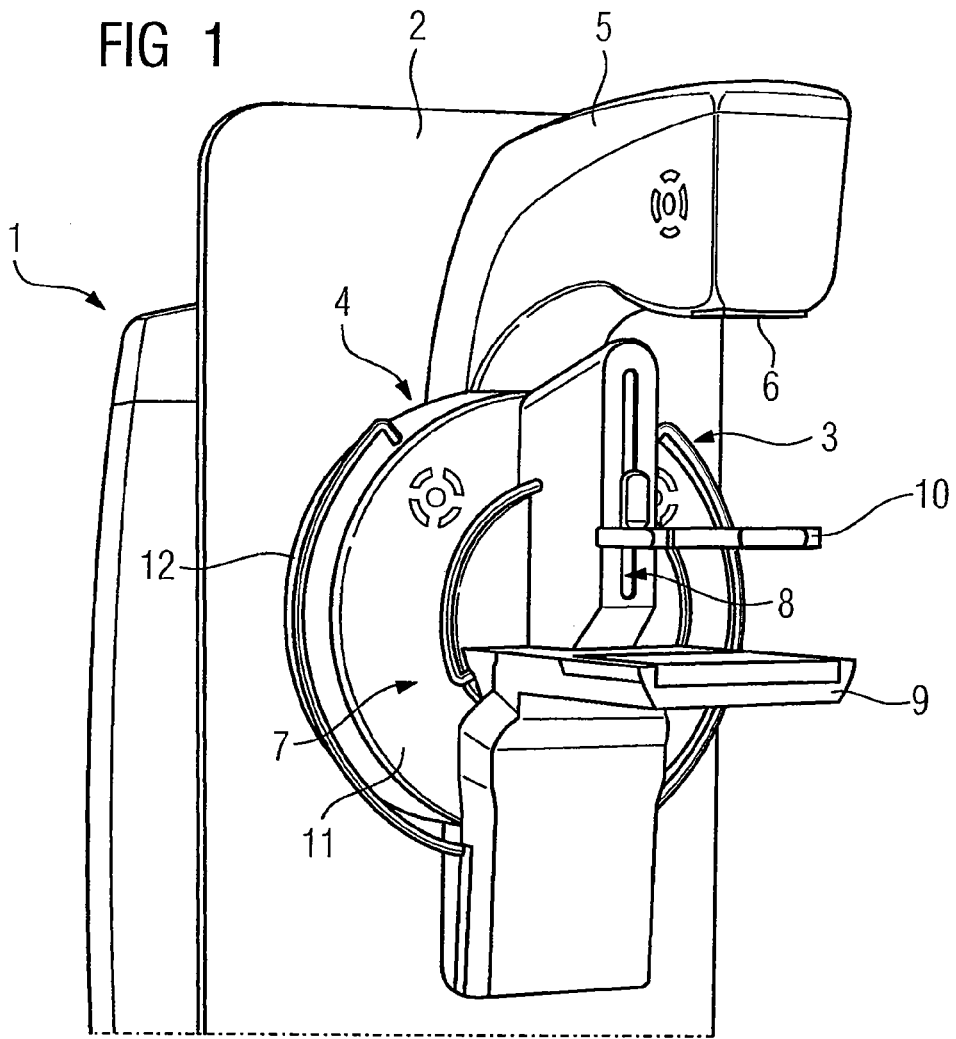
FIG. 1 shows an exemplary embodiment of a positioning device as part of a mammography device in a model 3D representation.

FIG. 1 shows a schematic three-dimensional view of a mammography device 1 at an angle from the side. The mammography device 1 includes a base body 2 and a positioning device 3, which is supported by the base body 2.

The positioning device 3 has a device support section 4, on which a radiation source 6 and other components, such as an electronics system or diaphragm, are fixedly attached by way of an angled device arm 5.

Figure 2:
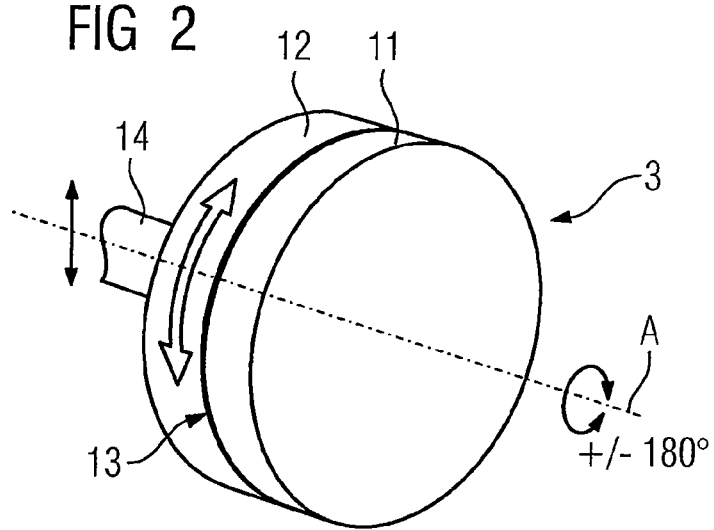
FIG. 2 shows the exemplary embodiment in FIG. 1 reduced to a schematic representation of an actuating section in order to illustrate the possible degree of freedom of the actuator.

The positioning device 3 includes an object support section 7, which is fixedly connected to an object holder 8. The object holder 8 has a base plate 9 for supporting the examination object, such as a female breast, and a pressure plate 10, which is arranged in parallel to the base plate 9. The pressure plate 10 can be displaced relative to the base plate 9, so that the examination object can be compressed. Optionally, a biopsy device for fine needle or punch biopsy, is arranged on the object support section 7, which is fixedly connected to the base plate 9 and has a positioning device for the fine needle and/or punching part. The object support section 7 includes a disk-like cover section 11 as a second body, which is arranged in parallel to the front side of the base body 2 and has a circular external contour in the projection on the base body 2. The cover section 11 is connected to the base body 2 by an axis of rotation 14 (FIG. 2). Depending on the embodiment of the positioning device 3, the cover section 11 is coupled to the axis of rotation 14 in a torque-proof fashion and is rotatably mounted hereupon. The rotational movement of the cover section 11 takes place about an axis A (FIG. 2), which is aligned parallel to the axis of rotation 14 (FIG. 2) and leads through an isocenter of the mammography device 1. The isocenter rests on the position of the subsequent center point of the examination object, for example, approximately 3 cm above the base plate 9. The object holder 8 and cover section 11 are connected to one another in a torque-proof fashion, so that a rotation of the cover section 11 leads to a rotation of the object holder 8.

The device support section 4 includes a rear annular body 12 as a first body, which is fixedly connected to the device arm 5 and is rotatably mounted on the axis of rotation 14 (FIG. 2). The cover section 11 and the rear annular body 12 are arranged congruent to one another and connect flush with one another laterally. The danger of crushing when rotating the device support section 4 or the object support section 7 is reduced. The outer diameter of the cover section 11 and/or the rear annular body 12 corresponds to the radial distance between the isocenter and the upper edge of the object holder 8. The distance between the isocenter and the radiation source 6 is bridged approximately at one half through the rear annular body 12 and at the other half through the device arm 5 so that the device arm 5 is comparatively short and compact and is embodied in an oscillation-safe fashion. Based on the axis A, the cover section 11 and/or rear annular body 12 can include a uniform weight distribution in the azimuthal direction. Alternatively, the rear annular body 12 can have a counter weight arranged diametrically with respect to the device arm 5, so that a counter torque is formed at the device arm 5.

FIG. 2 shows the positioning device 3 in FIG. 1 in an abstracted 3D representation at an angle from the side. In this representation, only the cover section 11 and the rear annular body 12 are shown, with a separation plane 13 being embodied herebetween. The cover section 11 and the rear annular body 12 can be rotated about the axis A by +/−180° using the axis of rotation 14, the axis A lying in the center axis of the axis of rotation 14. The rear annular body 12 is rotatably mounted about the axis A in a range of +/−25° relative to and decoupled from the front annular body 11. The entire positioning device 3 is accommodated in the base body 2 in a height-adjustable fashion, with the axis A and/or axis of rotation 14 being adjustable in the direction of the double arrow shown. For example, the entire positioning device 3 is adjustable in terms of height. The object holder 8 and handles and displays are arranged on the cover section 11 (as discussed in conjunction with FIG. 1) and a biopsy unit and/or enlargement table may be fastened to the cover section 11. The device arm 5 and the radiation source 6 can be fastened to the rear annular body 12. The cover section 11 and the rear annular body 12 together form a continuous cylinder or cone-shaped shell, so that no crushing regions are present particularly in the region of the separation plane 13.

Figure 3C:
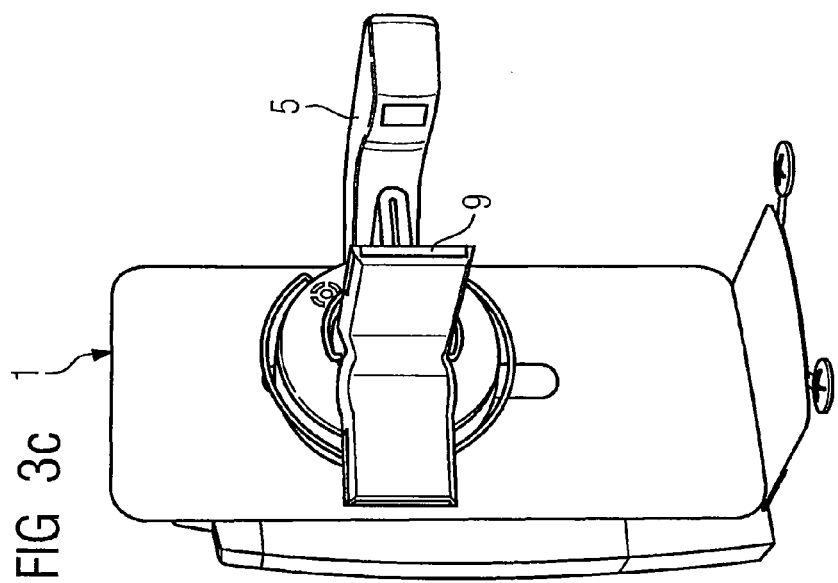
FIGS. 3a, b, c show the mammography device in FIG. 1 in three snapshots in different positions or settings of the positioning device.
Figure 3B:
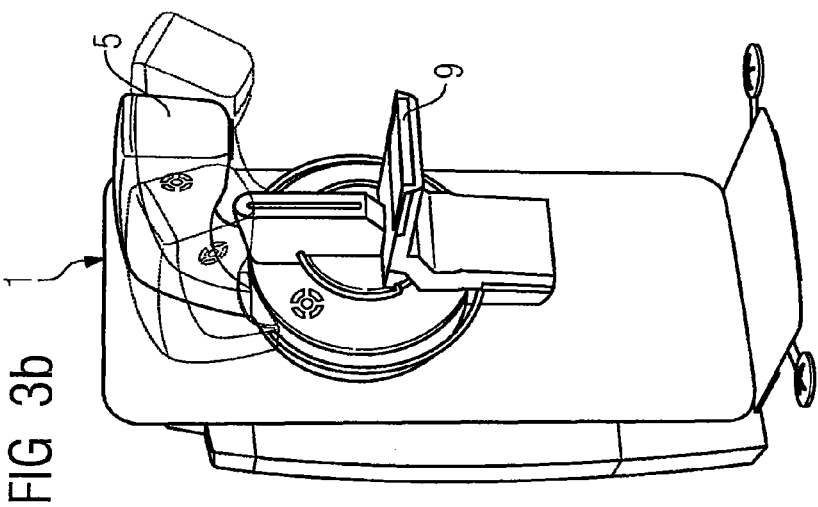
Figure 3A:
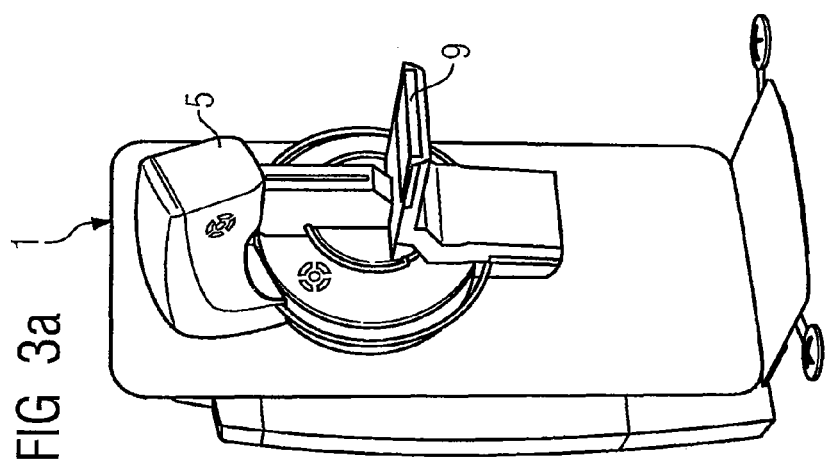

FIGS. 3a, b and c show snapshots of the mammography device 1 in FIG. 1 during different examination methods. FIG. 3a shows the mammography device 1 with a base plate 9 aligned horizontally thereto and a device arm 5 pivoted about approximately −15° in respect of the perpendicular during a stereotactic examination. The device arm 5 is pivoted about the isocenter.

FIG. 3b illustrates a tomosynthesis examination using the mammography device 1 in FIG. 1. With this examination method, the device arm 5 with the radiation source 6 is continuously pivoted, such as automatically, at an angular range from −25° to +25°, while the object holder 8 and the base plate 9 remain at the same time stationary. This recording method allows the examination object to be recorded in a manner similar to that using tomography.

FIG. 3c shows the mammography device 1 in FIG. 1 including in a setting, in which the base plate 9 is aligned at right angles and the device arm 5 and the radiation source 6 are likewise pivoted about +90° in respect of the perpendicular. Based on this setting, it is also possible to pivot the device arm 5 base plate 9 about up to +/−25° relative to the object holder 8.

Figure 4A:
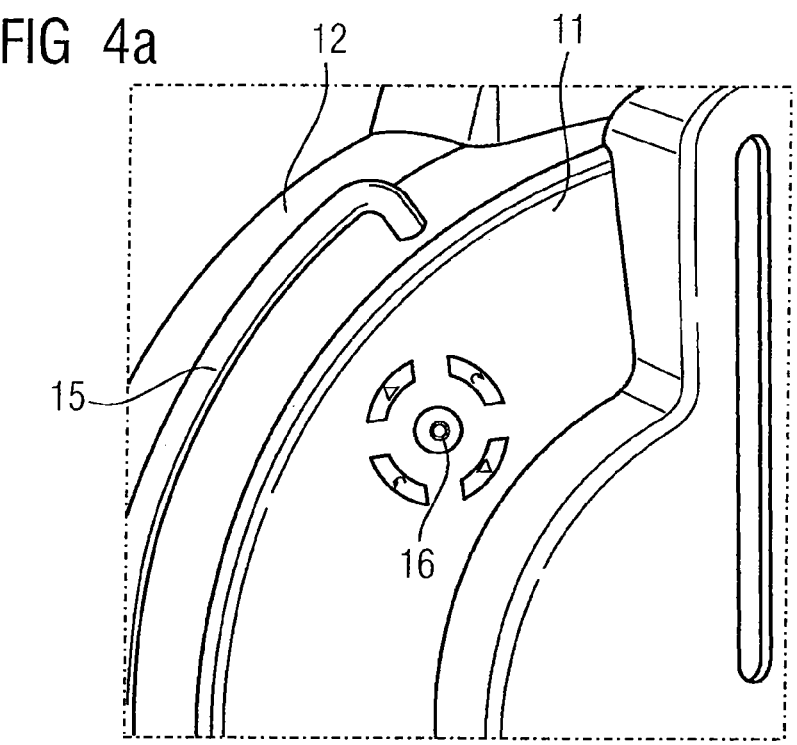
FIGS. 4a, b show enlarged cutout views of the positioning device to better represent integrated control elements on an annular "Doughnut section" of the positioning device.
Figure 4B:
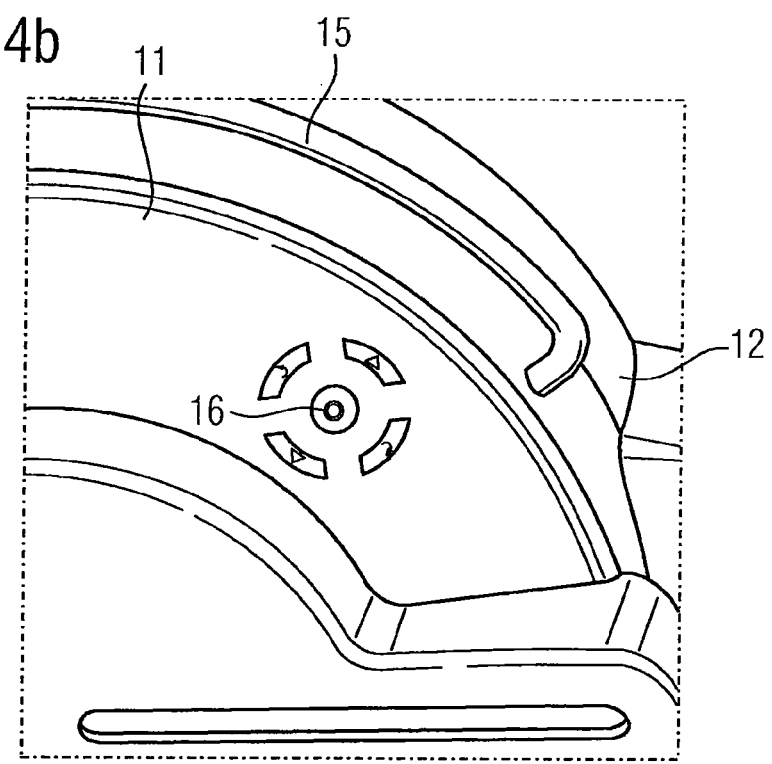

FIGS. 4a, b each show a detailed cutout of the mammography device 1 in FIG. 1. These detailed cutouts each show handles 15 and control buttons 16, which are attached to the front annular body 11 and include for instance the functions "Device on/off", "Rotate device left/right", "Light on/off". The control elements 16 are located on the front face of the front annular body 12, whereas the handles 15 are arranged on the radial exterior side thereof for instance. The handles 15 can be arranged, for example, radially and/or concentrically. All other positions (ML, MLO, etc.) of the positioning device 3 can be easily accessed by virtue of the concentric arrangement of the control elements 16.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A positioning device for relative positioning of a radiation source and an object holder of a mammography device, the positioning device comprising:
   a device support section that accommodates the radiation source,
   an object support section that accommodates the object holder, the object support section being connectable and/or connected to the mammography device by a connecting element,
   wherein the device support section is mounted such as to be able to rotate relative to the connecting element and to the object support section,
   wherein the device support section includes a device arm, the device arm comprising:
      a free end that holds the radiation source, and
      a hinged end comprising a first annular body and a through opening wherein, the connecting element protrudes through the opening, the opening surrounds the connecting element, or the connecting element protrudes through the opening and the opening surrounds the connecting element, and
   wherein the object support section includes a second annular body forming a cover section covering the first annular body, the first annular body and the second annular body being arranged congruent so that the circumferential surfaces of the first annular body and the second annular body are flush with each other, independent of the rotational position of the device support section with respect to the object support section.

2. The positioning device as claimed in claim 1, wherein the connecting element is an axis of rotation.

3. The positioning device as claimed in claim 2, wherein the axis of rotation or swivel axis enables a rotation of the object support section of up to +/−180°.

4. The positioning device as claimed in claim 1, wherein the first body is arranged between the mammography device and the second body.

5. The positioning device as claimed in claim 4, wherein the first annular body and the second annular body are arranged congruent or flush with one another perpendicular to a longitudinal extension of the connecting element.

6. The positioning device as claimed in claim 1, wherein the device support section and the object support section are rotatably arranged about a common center.

7. The positioning device as claimed in claim 1, wherein the device support section is operable to be pivoted up to about +/−25° relative to the object support section.

8. The positioning device as claimed in claim 1, wherein the connecting element is adjustable relative to the mammography device in terms of a height and a lateral position.

9. The positioning device as claimed in claim 1, wherein the object support section and the device support section include displays, handles, or control buttons.

10. The positioning device as claimed in claim 1, wherein the second annular body is a cover section or a ring.

11. The positioning device as claimed in claim 1, wherein the connecting element is adjustable relative to the mammography device in terms of a height or a lateral position.

12. The positioning device as claimed in claim 1, wherein the object support section or the device support section includes displays, handles, or control buttons.

* * * * *

UNITED STATES PATENT AND TRADEMARK OFFICE
CERTIFICATE OF CORRECTION

PATENT NO. : 7,885,379 B2  
APPLICATION NO. : 12/162282  
DATED : February 8, 2011  
INVENTOR(S) : Oliver Meer and Martin Ramsauer Page 1 of 1

It is certified that error appears in the above-identified patent and that said Letters Patent is hereby corrected as shown below:

In the claims:
Column 6, claim 4, line 38, please add "annular" between "first" and "body"
Column 6, claim 4, line 39, please add "annular" between "second" and "body"

Signed and Sealed this
Eighth Day of March, 2016

Michelle K. Lee
*Director of the United States Patent and Trademark Office*